United States Patent [19]
Hein et al.

[11] Patent Number: 6,088,619
[45] Date of Patent: Jul. 11, 2000

[54] DEVICE AND METHOD FOR AIDING THE POSITIONING OF AN EXTERNAL PART RELATIVE TO AN IMPLANTABLE PART OF A CHARGING SYSTEM FOR AN IMPLANTABLE MEDICAL DEVICE

[75] Inventors: Walter Hein, Germering; Reinhard Mayer, München, both of Germany

[73] Assignee: IMPLEX Aktiengesellschaft Hearing Technology, Ismaning, Germany

[21] Appl. No.: 09/371,272

[22] Filed: Aug. 10, 1999

[30] Foreign Application Priority Data

Feb. 26, 1999 [DE] Germany .............................. 199 08 438

[51] Int. Cl.[7] .................................................. A61N 1/08
[52] U.S. Cl. ................................................................ 607/61
[58] Field of Search ................................ 607/33, 55, 61, 607/62, 32, 30

[56] References Cited

U.S. PATENT DOCUMENTS

| | | |
|---|---|---|
| 5,277,694 | 1/1994 | Leysieffer et al. . |
| 5,279,292 | 1/1994 | Baumann et al. . |
| 5,690,693 | 11/1997 | Wang et al. . |
| 5,814,095 | 9/1998 | Muller et al. . |

OTHER PUBLICATIONS

Leysieffer et al., A Completely Implantable Hearing System for the Hearing Impaired: TICA LZ 3001, HNO 46:853–863, (1998).

P.E.K. Donaldson, Power for Neurological Prostheses: A Simple Inductive R.F. Link with Improved Performance, J. Biomed. Eng., vol. 9, (Jul., 1987).

*Primary Examiner*—Scott M. Getzow
*Attorney, Agent, or Firm*—Nixon Peabody LLP; David S. Safran

[57] ABSTRACT

The invention relates to a device and a method for aiding the positioning of an external transmitting part relative to an implantable receiving part of a charging system for charging a rechargeable power source of an implantable medical device such as an implantable hearing aid. The external transmitting and the implantable receiving part each has a resonant circuit with a transmitting coil and a receiving coil respectively. These coils can be inductively coupled to one another by corresponding manual positioning of the external transmitting part for transcutaneous power transmission. The external transmitting part is provided with an oscillator which is connected to the transmitting resonant circuit and the oscillator has a resonant frequency which shifts as a function of the coupling between the transmitting coil and the receiving coil. The external transmitting part is also provided with a measurement arrangement for determining the frequency detuning of the oscillator and an evaluation arrangement for outputting a positioning signal as a function of the determined frequency detuning of the oscillator.

25 Claims, 2 Drawing Sheets and the receiving part and makes it possible to arrange all the components necessary to aid in positioning on the transmitting side, i.e. externally. The device and method of the present invention also remains serviceable when the implanted medical device or its telemetry arrangement have failed due to drainage of the implanted power source and if (for example) based on charging current control or limitation of the current flowing through the transmitting coil, there is no clear indication for achieving a position which is optimum for the charging process, as long as the resonant properties of the receiving resonant circuit are preserved.

DEVICE AND METHOD FOR AIDING THE POSITIONING OF AN EXTERNAL PART RELATIVE TO AN IMPLANTABLE PART OF A CHARGING SYSTEM FOR AN IMPLANTABLE MEDICAL DEVICE

BACKGROUND OF THE INVENTION

1. Field of the Invention

The present invention relates to a device and method or aiding the positioning of an external part relative to an implantable part of a charging system for charging a rechargeable power source of an implantable medical device. In particular the present invention relates to such devices and method where an external transmitting part and an internal receiving part are provided with a resonant circuits with coils which can be inductively coupled to one another for transcutaneous power transmission by manual positioning of the external transmitting part.

2. Description of Related Art

A device and a process of this general type are known from U.S. Pat. No. 5,279,292. In this reference, a telemetry circuit is assigned to the charging electronics of a receiving part which delivers a signal to the outside which is characterized by the mutual alignment of the transmitting and receiving part (such as those discussed in Leysieffer et al. "*A completely implantable hearing system for the hearing impaired: TICA LZ3001*" in HNO. 46:853–863 (1998)), thereby providing to the implant wearer information relating to the positioning of the transmitting part relative to the receiving part during the charging process through acoustic signals which are supplied to the acoustic signal path of a hearing aid. In another known device for aiding the positioning of a charging system for implantable medical device as shown in U.S. Pat. No. 5,690,693, the correct mutual alignment of the transmitting part and receiving part is optically displayed on the transmitting part based on the current flowing through the transmitting coil.

SUMMARY OF THE INVENTION

The primary object of the present invention is to provide a device and a method for aiding the manual positioning of an external transmitting part in a charging system for implantable medical devices which can provide reliable and obvious positioning signals to the implant wearer.

This object is achieved in a device of the above mentioned type including an external transmitting part having an oscillator which is connected to a transmitting resonant circuit, the oscillator having a resonant frequency which shifts as a function of the coupling between the transmitting and receiving coil. The external transmitting part may also be provided with a measurement arrangement for measuring the frequency detuning of the oscillator and an evaluation arrangement for outputting a positioning signal as a function of the ascertained frequency detuning of the oscillator.

According to the method of the present invention, there is provided an oscillator in the external transmitting part which is connected to a transmitting resonant circuit, the oscillator having a resonant frequency which shifts as a function of the coupling between a transmitting and a receiving coil. The frequency detuning of the oscillator which is indicative of the alignment of the transmitting part relative to the receiving part is measured and depending on the ascertained frequency detuning, a positioning signal is outputted which allows the evaluation of the positioning.

The device and method in accordance with the present invention works without telemetry between the transmitting Fundamentally, in an oscillator of the type described here, the relative motion of the transmitting and receiving coils is detuned in all three dimensional axes (X, Y, and Z). Since during the charging process, the transmitting part is seated on the skin over the receiving part, the axis Z which indicates the distance of the coils to one another, is defined for the implant wearer by the thickness of the skin or tissue over the implant and can be assumed to be constant for the positioning process in the individual patient.

More specifically, in one embodiment of the present invention, the external transmitting part may have an oscillator such as a Donaldson oscillator. Such an oscillator is know and described in the article of P. E. K. Donaldson "*Power for Neurological Prostheses: A Simple Inductive R.F. Link with Improved Performance*", J. Biomed. Eng. Vol. 9 (July, 1987). One typical feature of such an oscillator is that its resonant frequency is shifted as a function of the coupling between the transmitting coil and the receiving coil. The shift increases with increasing coupling between the transmitting and receiving circuit. Since coupling is greatest in aligned coils, the relative positioning of the coils can be determined from the amount of detuning. In the case of a Donaldson oscillator, the charging current flowing instantaneously in the receiving resonant circuit becomes part of the detuning such that with increasing charging state of the rechargeable power source, the detuning decreases. But since the positioning phase is relatively short (generally at most one minute), the change of the charging current can be ignored for positioning purposes, especially since generally, each charging process begins with the maximum possible charging current and the charging control circuit controls the current only in a later phase of the charging process.

The transmitting resonant circuit and the receiving resonant circuit are preferably made as series resonant circuits. Furthermore, the transmitting coil and receiving coil also preferably serve as coils for the respective transmitting resonant circuit and receiving resonant circuit.

To use frequency detuning of the oscillator as a positioning aid, the sign of the detuning should be explicit. In addition, when the implant is encapsulated in a metal jacket, for example a titanium jacket, it is desirable to be able to distinguish the resulting detuning in the coupling between the transmitting coil and the receiving coil from the detuning in coupling between the transmitting coil and the metal jacket. This can be easily attained since the resonant frequency of the transmitting resonant circuit differs slightly from the resonant frequency of the receiving resonant circuit. In particular, the difference may be preferably roughly 0.5 to 3%. In one embodiment, the resonant frequency of the transmitting resonant circuit is less than the resonant frequency of the receiving resonant circuit by preferably 1 to 2%. In this design, the frequency deviation becomes negative as the coupling of the two circuits increases and the frequency deviation becomes positive when the transmitting coil is coupled to the metal jacket of the implantable receiving part.

The measurement arrangement can have a counting circuit which counts the oscillations of the oscillator per unit of time for determining the frequency detuning of the oscillator. One such counting circuit can be built as a discrete circuit or can preferably be integrated into the function of a microcontroller of the external transmitting part.

For determining the value of the frequency deviation, the measurement arrangement can be provided with a means for measuring the fundamental frequency of the oscillator in the uncoupled state and for cyclic comparison measurement and difference formation in the coupled state. According to one modified embodiment of the invention, the measurement arrangement can be provided with a means for computing the difference of two succeeding frequency measurement values.

In another alternative embodiment, the measurement arrangement can also have a means for measuring the period of oscillator oscillations which can be used to determine the frequency detuning of the oscillator. The value of the frequency deviation can be determined similar to the above except that the period of the oscillations is measured. This means that there can be means for measuring the basic period of the oscillator in the uncoupled state and for cyclic comparison measurement and difference formation in the coupled state, or the measurement arrangement can be equipped with a means for computing the difference of two succeeding period values. Of course, there can be a discrete circuit provided to measure the period of the oscillator oscillations. But preferably, the means for measuring the period of the oscillator oscillations are integrated into the function of the microcontroller of the transmitting part.

Measurements are evaluated preferably by a program executed and controlled by the microcontroller. One or more threshold values and/or a self-adapting algorithm can be programmed into the microcontroller for evaluating the measurement and to determine whether a positioning signal which indicates good or poor positioning should be provided. The evaluation arrangement can especially be designed such that it delivers optical and/or acoustic display signals. For example, the optical signaling on the transmitting part can be provided by a duo-LED unit which lights red, orange or green depending on the respective alignment of the transmitting coil and the receiving coil. Alternatively, for acoustic signaling, the oscillator frequency can be mixed with a fixed reference frequency such that the mixed frequency yields an audible tone, the level of this tone depending on the quality of the coupling between the transmitting coil and the receiving coil. The tone level is set to maximum or minimum depending on the circuit design by the positioning of the transmitting coil relative to the receiving coil and may be set to vary accordingly.

Within the framework of this invention, measurement, evaluation, and signaling are done in real time. This means that the user acquires a return report, especially an optical and/or acoustic return message as a positioning aid, during positioning motion.

The above object, features and advantages of the present invention will become more apparent form the following detailed description of the preferred embodiments of this invention when viewed in conjunction with the accompanying drawings.

DETAILED DESCRIPTION OF THE INVENTION

Figure 1:
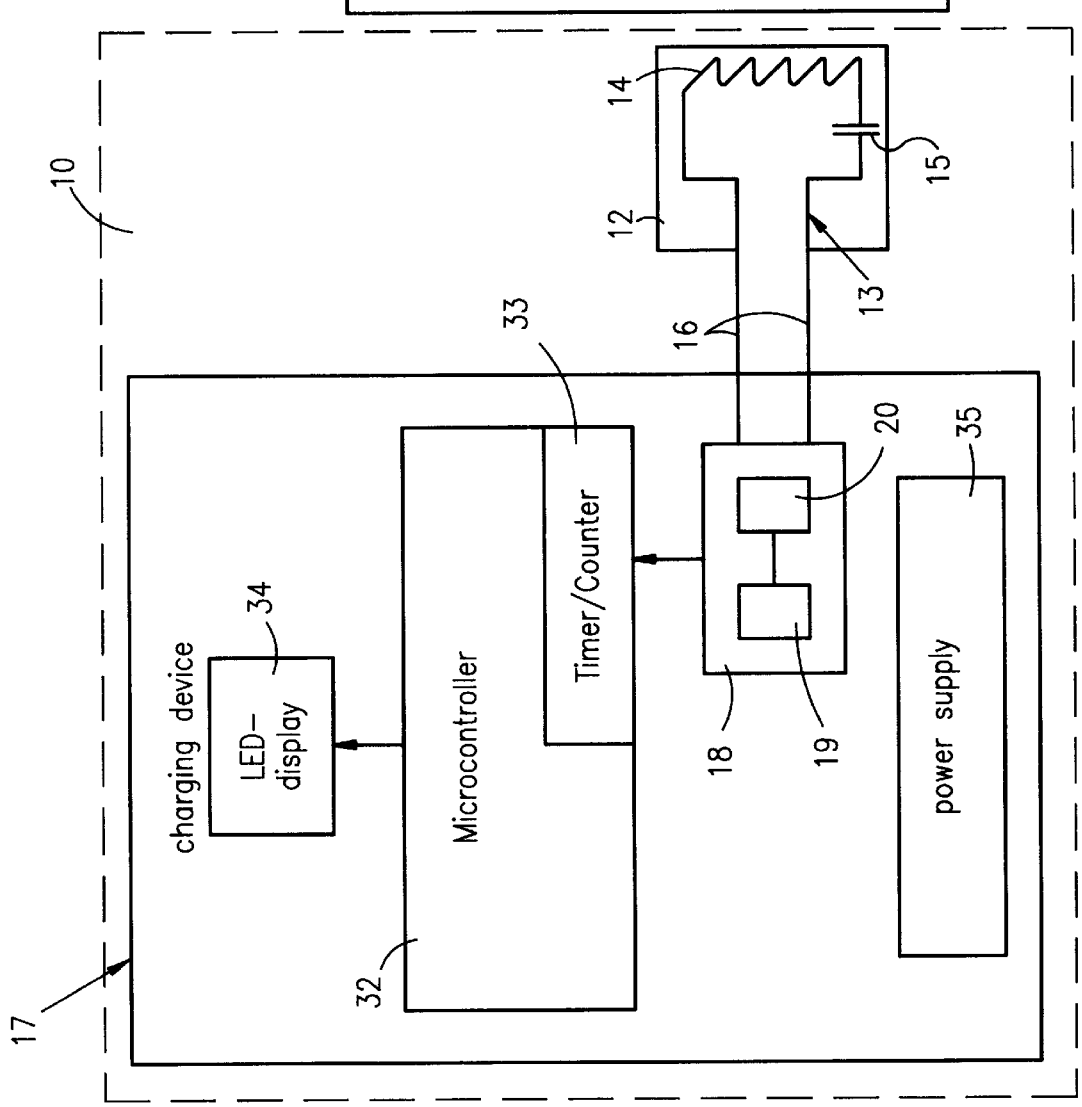
FIG. 1 shows a schematic block diagram of one embodiment of the present invention.
Figure 2:
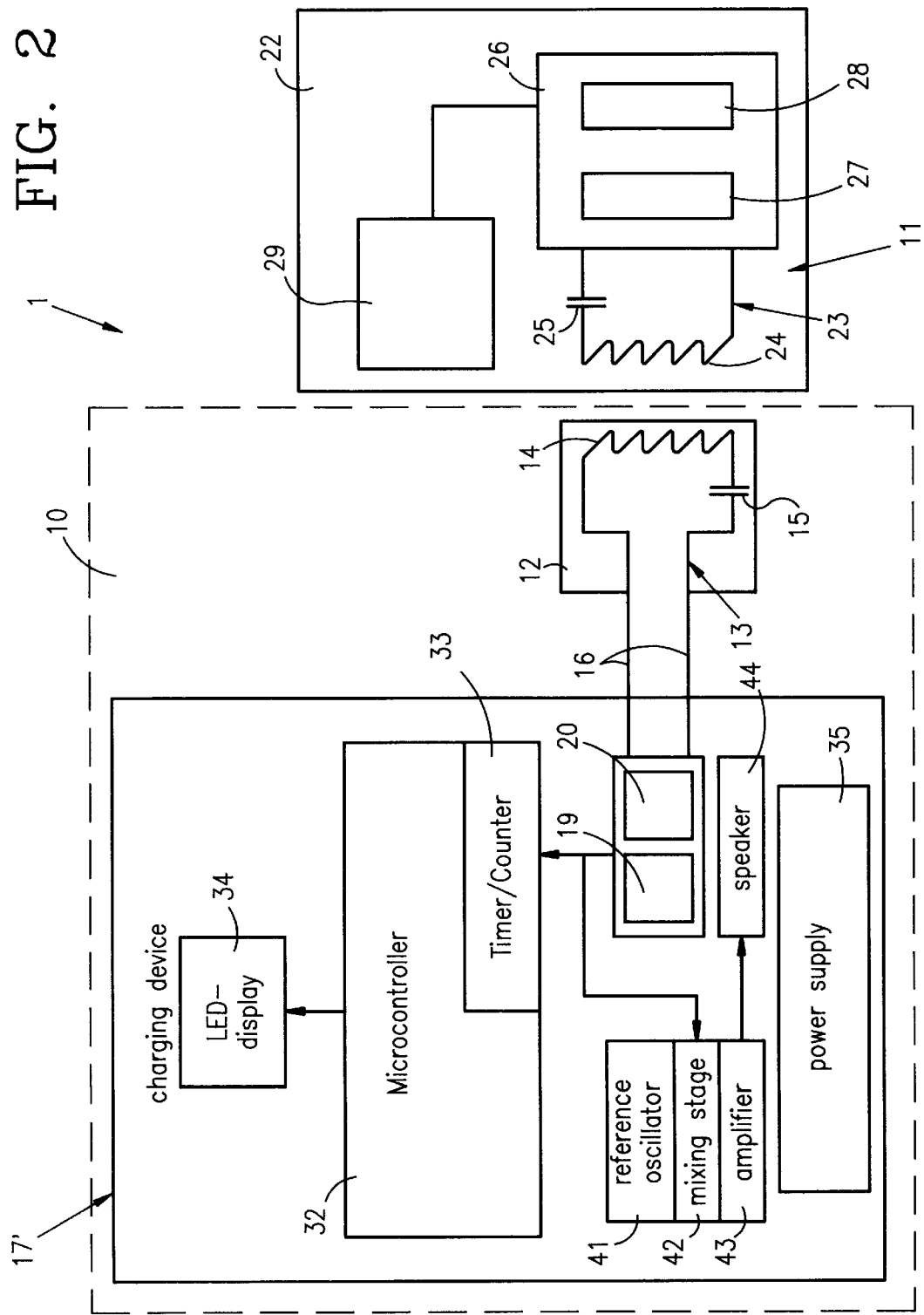
FIG. 2 shows a schematic block diagram of an alternative embodiment of the present invention.

FIGS. 1 & 2 schematically illustrate a device in accordance with two embodiments of the present invention for aiding the positioning of an external part relative to an implantable part of a charging system for charging a rechargeable power source of an implantable medical device. The charging system 1 in accordance with one embodiment of the present invention, as shown in FIG. 1, has an external transmitting part 10 and an implantable receiving part 11. The external transmitting part 10 includes a charging head 12 which contains a transmitting resonant circuit 13 with a transmitting coil 14 and a transmitting circuit capacitor 15 connected in series thus forming a series resonant circuit. In addition to forming part of the transmitting resonant circuit 13, the transmitting coil 14 functions as a transmitter for the external transmission part 10. The charging head 12 is connected via an electrically conductive link such as cables 16 to an output of a charging device 17 which is part of the external transmitting part 10. In particular, the transmitting resonant circuit 13 is connected to a transmitting switching stage 18 which may include an oscillator such as a Donaldson oscillator 19 and a transmission end stage 20 connected downstream of the Donaldson oscillator 19.

The implantable receiving part 11 in accordance with the present embodiment may be a component of an implantable medical device generically labeled 22. The implantable receiving part 11 includes a receiving resonant circuit 23 with a receiving coil 24 and a receiving circuit capacitor 25 connected in series, thus forming a series resonant circuit. In addition to forming a part of the receiving resonant circuit 23, the receiving coil 24 serves as a receiver for the implantable receiving part 11. The receiving resonant circuit 23 is connected to an input of a receiving switching stage 26 which includes a charging control circuit 27 and a power source 28 downstream of the charging control circuit 27. The power source 28 may be in the form of a rechargeable DC voltage source including a rechargeable battery. The power source 28 is used to supply power to an active medical implant 29 such as a hearing aid. The power source 28 can be designed as a power supply module as shown in an commonly owned, co-pending U.S. patent application Ser. No. 09/359,050 claiming priority of the German patent application, 198 37 912.9-45 which is incorporated herein by reference. The charging control circuit 27 and the charging process can be executed according to the commonly owned, copending U.S. patent application Ser. No. 09/311, 566 filed on May 14, 1999 which is also incorporated herein by reference. The active medical implant 29 such as a hearing aid, can be made for direct mechanical excitation of the middle ear or inner ear of the implant wearer. One such hearing aid is shown, for example, in U.S. Pat. No. 5,277, 694, U.S. Pat. No. 5,814,095, and in the aforementioned article by Leysieffer et al. "A completely implantable hearing system for the hearing impaired: TICA LZ 3001", HNO 46:853–863 (1998). Therefore, the charging control circuit 27 and the active medical implant 29 need not be discussed in further detail here.

The charging device 17 also includes a micro-controller 32 which has a timer/counter 33, a LED display 34 connected to the microcontroller 32, and a power supply 35 for providing power to the components of the transmitting part 10.

To recharge the power source 28 of the implantable medical device 22, the charging head 12 of the external transmitting part 10 is placed on the skin of the implant wearer and is manually positioned such that the transmitting coil 14 is aligned as much as possible with the receiving coil 24 so that the two coils together, form the primary and secondary circuit of a HF transformer and the receiving coil 24 can acquire electromagnetic energy from the transmitting coil 14.

The positioning aid provided in the illustrated embodiment of the present invention operates based on the fact that the resonant frequency of the Donaldson oscillator 19 shifts as a function of the inductive coupling between the transmitting resonant circuit 13 and the receiving resonant circuit 23 such that detuning of the Donaldson oscillator 19 increases as coupling between the transmitting coil 14 and the receiving coil 24 increases. Since the inductive coupling is greatest when the transmitting coil 14 and the receiving coil 24 are aligned, the relative position of these coils 14, 24 can be derived from the amount of detuning present. Admittedly, the detuning depends fundamentally on the relative displacement of the transmitting coil 14 and the receiving coil 24 in all three axial directions. When the charging head 12 is placed on the skin however, the distance between the coils in one axial direction is dictated in by the thickness of the skin or the tissue over the implantable medical device 22 and can be regarded as a constant. In the Donaldson oscillator 19, charging current flowing instantaneously in the receiving resonant circuit 23 becomes part of the detuning such that with increasing charging of the power source 28, the detuning decreases. But since the positioning phase is relatively short (generally at most one minute), the change of charging current can be ignored for positioning purposes, especially since generally, each charging process begins with the maximum possible charging current and the charging control circuit 27 controls the current only in a later phase of the charging process.

To use frequency detuning of the Donaldson oscillator 19 as a positioning aid, the sign of the detuning should be explicit. In addition, when the implantable medical device 22 is encapsulated in a metal jacket (not shown), for example a titanium jacket, it is desirable to be able to distinguish the resulting detuning in the coupling between the transmitting coil 14 and the receiving coil 24 from the detuning in coupling between the transmitting coil 14 and the metal jacket (not shown). This can be easily attained since the resonant frequency of the transmitting resonant circuit 13 can be made to differ slightly from the resonant frequency of the receiving resonant circuit 23. In particular, the difference may be preferably roughly 0.5 to 3%. In one embodiment, the resonant frequency of the transmitting resonant circuit 13 is made to be less than the resonant frequency of the receiving resonant circuit 23 by preferably 1 to 2%. In this design, the frequency deviation becomes negative as the coupling of the two circuits increases and the frequency deviation becomes positive when the transmitting coil 14 is coupled to the metal jacket (not shown) of the implantable medical device 22.

The frequency detuning of the Donaldson oscillator 19 can be determined by a measurement arrangement such as a microcontroller 32 which may include an integral counting circuit such as the timer/counter 33 which counts the oscillations of the Donaldson oscillator 19 per unit of time. Of course, in an alternative embodiment, the counting circuit can be built as a discrete circuit. Preferably however, the counting circuit may be integrated into the function of the microcontroller 32 as shown in the timer/counter 33 of FIG. 1. The value of the frequency deviation can be determined by:

(a) measuring the fundamental frequency of the Donaldson oscillator 19 in the uncoupled state and cyclic comparison measurement and difference formation when the transmitting coil 14 and the receiving coil 24 are coupled; or in an alternative embodiment, (b) computing the difference between two frequency measurement values which succeed one another during positioning (rise).

Alternatively, the frequency detuning of the Donaldson oscillator 19 can also be determined by measuring the period of the oscillator's oscillations. A discrete circuit (not shown) may be provided to accomplish this. Preferably however, such period measurement may be integrated into the function of the microcontroller 32. The value of the frequency deviation can be determined in a manner analogous to the aforementioned alternatives (a) and (b) except that the period of the oscillator's oscillations is measured. This means that the measurement arrangement such as the microcontroller 32 may be provided with a means for measuring the basic period of the Donaldson oscillator 19 in the uncoupled state and for cyclic comparison measurement and difference formation in the coupled state, or the measurement arrangement can be equipped with means for computing the difference of two succeeding period values.

Preferably, the above explained measurements are evaluated by an evaluation arrangement for outputting a positioning signal as a function of the ascertained frequency detuning of said oscillator. In the illustrated embodiment, an evaluation arrangement such as a program executed and controlled by the microcontroller 32 is used. In this regard, one or more threshold values and/or a self-adapting algorithm can be programmed into the microcontroller 32 specifically to evaluate the measurement and to determine whether a positioning signal which indicates good or poor positioning should be provided. Of course, the evaluation arrangement can be built as a discrete circuit but preferably, the microcontroller 32 may be used for this purpose.

In the above discussed embodiment of FIG. 1, the evaluation arrangement such as the microcontroller 32 may then trigger a LED display 34 according to the results of the aforementioned evaluation of the measurement which will provided an indication whether the positioning is good or poor. The LED display 34 may be a duo-LED display unit, for example, which lights red, orange, or green depending on the trigger signal of the microcontroller 32 and thus, clearly indicating to the implant wearer when the charging head 12 assumes a position in which satisfactory coupling of the transmitting coil 14 and the receiving coil 24 is established. It goes without saying that other optical display units may be provided. Furthermore, the proper positioning may also be indicated by a color change of a display and/or by triggering blinking at different rates.

The embodiment of FIG. 2 is very similar to the above discussed embodiment of FIG. 1 and operates similarly except that an alternative embodiment of the charging device 17' is shown which additionally includes a reference oscillator 41, a mixing stage 42, an amplifier 43 and a speaker 44. In this embodiment, the reference oscillator 41 generates a fixed reference frequency which is mixed in the mixing stage 42 with the frequency of the Donaldson oscillator 19 such that a signal in the audible frequency range is formed from the mixed frequency. This signal is amplified in an amplifier 43 and is delivered as an audible tone by the speaker 44. The tone level in this embodiment depends on the quality of coupling between the transmitting coil 14 and the receiving coil 24 and thus, can be used as an indicator for the relative positioning of the charging head 12 and the implantable receiving part 11. The tone level is set to maximum or minimum depending on the circuit design by the positioning of the transmitting coil 14 relative to the receiving coil 14 and may be set to vary accordingly.

While various embodiments in accordance with the present invention have been shown and described, it is understood that the invention is not limited thereto. The present invention may be changed or modified as known to those skilled in the art. Therefore, this invention is not limited to the details shown and described herein, and includes all such changes and modifications as are encompassed by the scope of the appended claims.

We claim:

1. Device for aiding the positioning of an external part relative to an implantable part of a charging system for charging a rechargeable power source of an implantable medical device comprising,
   an external transmitting part including a transmitting resonant circuit with a transmitting coil;
   an implantable receiving part including a receiving resonant circuit with a receiving coil, said transmitting coil being adapted to be inductively coupled to said receiving coil by manual positioning of said external transmitting part thereby allowing transcutaneous power transmission;
   an oscillator connected to said transmitting resonant circuit, said oscillator having a resonant frequency which shifts as a function of the inductive coupling between said transmitting coil and said receiving coil;
   a measurement arrangement for determining frequency detuning of said oscillator; and
   an evaluation arrangement for outputting a positioning signal as a function of the determined frequency detuning of said oscillator.

2. Device of claim 1, wherein said oscillator is a Donaldson oscillator.

3. Device of claim 1, wherein said transmitting resonant circuit and said receiving resonant circuit are series resonant circuits.

4. Device of claim 1, wherein a coil in said transmitting resonant circuit functions as said transmitting coil.

5. Device of claim 1, wherein a coil in said receiving coil functions as said receiving coil.

6. Device of claim 1, wherein a resonant frequency of said transmitting resonant circuit differs slightly from a resonant frequency of said receiving resonant circuit.

7. Device of claim 6, wherein the resonant frequency of said transmitting resonant circuit is lower than the resonant frequency of said receiving resonant circuit.

8. Device of claim 6, wherein the resonant frequency of said transmitting resonant circuit differs from the resonant frequency of said receiving resonant circuit between 0.5 to 3 percent.

9. Device of claim 6, wherein the resonant frequency of said transmitting resonant circuit differs from the resonant frequency of said receiving resonant circuit between 1 to 2 percent.

10. Device of claim 1, wherein said measurement arrangement includes a counting circuit which counts oscillations of said oscillator per unit of time.

11. Device of claim 10, wherein said external transmitting part includes a microcontroller and said counting circuit is integrated therein.

12. Device of claim 10, wherein said measurement arrangement includes a means for measuring a fundamental frequency of said oscillator in an uncoupled state and for cyclic comparison measurement and difference formation in a coupled state.

13. Device of claim 10, wherein said measurement arrangement includes a means for computing a difference between two succeeding frequency measurement values.

14. Device of claim 1, wherein the measurement arrangement includes a means for measuring a period of oscillations of said oscillator.

15. Device of claim 14, wherein said external transmitting part includes a microcontroller with a means for measuring the period of oscillations of said oscillator integrated therein.

16. Device of claim 14, wherein said measurement arrangement includes a means for measuring a basic period of oscillations of said oscillator in an uncoupled state and for cyclic comparison measurement and difference formation in a coupled state.

17. Device of claim 14, wherein said measurement arrangement includes a means for computing a difference between two succeeding period measurement values.

18. Device of claim 1, wherein said external transmitting part includes a microcontroller with an evaluation arrangement integrated therein.

19. Device of claim 18, wherein at least one of a threshold value and a self-adapting algorithm are programmed into said microcontroller for evaluating at least one of a frequency measurement value and a period measurement value.

20. Device of claim 19, wherein said evaluation arrangement has means for delivering signals for at least one of an optical display and an acoustic speaker.

21. A method for aiding the positioning of an external part relative to an implantable part of a charging system for charging a rechargeable power source of an implantable medical device comprising the steps of:
    providing an external transmitting part including a transmitting resonant circuit with a transmitting coil;
    providing an implantable receiving part including a receiving resonant circuit with a receiving coil;
    inductively coupling said transmitting coil with said receiving coil by positioning said external transmitting part to allow transcutaneous power transmission;
    providing an oscillator connected to said transmitting resonant circuit, said oscillator having a resonant frequency which shifts as a function of the inductive coupling between said transmitting coil and said receiving coil;
    determining frequency detuning of said oscillator; and
    outputting a positioning signal as a function of the determined frequency detuning of said oscillator thereby allowing evaluation of the positioning.

22. A method of claim 21, further comprising the step of comparing the frequency detuning in the coupled state with frequency detuning of said oscillator in an uncoupled state;
    wherein the frequency detuning in the coupled state and the uncoupled state is determined by counting oscillations of said oscillator per unit of time.

23. A method of claim 21, further comprising the step of comparing the frequency detuning in the coupled state with frequency detuning of said oscillator in an uncoupled state;
    wherein the frequency detuning in the coupled state and the uncoupled state is determined by measuring periods of the oscillations of said oscillator.

24. A method of claim 21, further comprising the step of providing at least one of an optical signal and an acoustic signal which is dependent on the determined frequency detuning and serves as a positioning aid signal.

25. A method of claim 24, further comprising the step of mixing an oscillator frequency with a fixed reference frequency in a manner that a resulting mixed frequency yields an audible tone;

wherein a level of the audible tone depends on the quality of the inductive coupling between said transmitting coil and said receiving coil and is set by positioning movements of said transmitting coil relative to said receiving coil.

* * * * *